United States Patent
Lytvynenko et al.

(10) Patent No.: US 9,726,598 B2
(45) Date of Patent: Aug. 8, 2017

(54) METHOD AND DEVICE FOR CHARACTERISING A FLUID MEDIUM USING A PHOTOELECTRIC TRANSDUCER

(71) Applicants: CENTRE NATIONAL DE LA RECHERCHE SCIENTIFIQUE, Paris (FR); ECOLE CENTRALE DE LYON, Ecully (FR); INSTITUT NATIONAL DES SCIENCES APPLIQUEES DE LYON, Villeurbanne (FR); UNIVERSITE CLAUDE BERNARD LYON I, Villeurbanne (FR); UNIVERSITE T. CHEVTCHENKO DE KIEV, Kiev (UA)

(72) Inventors: Sergeii Lytvynenko, Kiev (UA); Dmytro Beilobrov, Kiev (UA); Volodymyr Lysenko, Villeurbanne (FR); Valeriy Skryshevskyy, Kiev (UA)

(73) Assignees: Centre National de la Recherche Scientifique, Paris (FR); Ecole Centrale de Lyon, Ecully (FR); Institut National des Sciences Appliquees de Lyon, Villeurbanne (FR); Universite Claude Bernard Lyon I, Villeurbanne (FR); Universite T. Chevtchenko de Kiev, Kiev (UA)

( * ) Notice: Subject to any disclaimer, the term of this patent is extended or adjusted under 35 U.S.C. 154(b) by 9 days.

(21) Appl. No.: 14/654,617

(22) PCT Filed: Dec. 17, 2013

(86) PCT No.: PCT/FR2013/053139

§ 371 (c)(1),
(2) Date: Jun. 22, 2015

(87) PCT Pub. No.: WO2014/102485

PCT Pub. Date: Jul. 3, 2014

(65) Prior Publication Data

US 2015/0316470 A1 Nov. 5, 2015

(30) Foreign Application Priority Data

Dec. 27, 2012 (FR) .................................... 12 62884

(51) Int. Cl.
*G01N 21/27* (2006.01)
*G01N 21/31* (2006.01)
*G01N 21/17* (2006.01)

(52) U.S. Cl.
CPC ......... *G01N 21/27* (2013.01); *G01N 21/1717* (2013.01); *G01N 21/31* (2013.01); *G01N 2021/1719* (2013.01); *G01N 2201/061* (2013.01)

(58) Field of Classification Search
CPC ............. G01N 27/228; G01N 33/0047; G01N 27/221; G01N 2027/222; G01N 21/1717;
(Continued)

(56) References Cited

U.S. PATENT DOCUMENTS 4,240,747 A * 12/1980 Harmer ................ G01N 21/431
250/227.25
4,836,012 A 6/1989 Doty et al.
(Continued)

FOREIGN PATENT DOCUMENTS

JP 2004-177384 6/2004
JP 2005-024286 1/2005

OTHER PUBLICATIONS

Wagner et al., "A high-density multi-point . . . array and FPGA control", Science and Actuators B: Chemical, 2011, pp. 124-128.
(Continued)

*Primary Examiner* — Sang Nguyen
(74) *Attorney, Agent, or Firm* — Clark & Brody

(57) ABSTRACT

A device for characterizing a fluid medium with the help of a photoelectric transducer comprises at least one semiconductor substrate possessing at least one space charge zone
(Continued)

and presenting a reception surface for receiving the fluid medium in order to constitute an interface between the substrate and the fluid medium, a production system for producing a spot light beam that is amplitude-modulated and that lights at least one zone of the interface through the fluid medium, a measurement system for measuring values of a photoelectric magnitude delivered while performing the lighting so as to create a matrix of values of the photoelectric magnitude, and a processor system for processing values of the photoelectric magnitude delivered by the measurement system and adapted to use the matrix to determine an electronic signature characteristic of the fluid medium.

17 Claims, 9 Drawing Sheets

(58) Field of Classification Search
CPC .................. G01N 21/31; G01N 21/27; G01N 2021/1719; G01N 2201/061
See application file for complete search history.

(56) References Cited

U.S. PATENT DOCUMENTS

| | | | | |
|---|---|---|---|---|
| 5,098,657 | A | * | 3/1992 | Blackford ............ G01N 15/065 239/74 |
| 5,369,495 | A | | 11/1994 | Lagowski |
| 5,659,129 | A | * | 8/1997 | Asoyan ................ G01N 29/036 73/54.25 |
| 2006/0042354 | A1 | | 3/2006 | Moritz et al. |
| 2015/0355125 | A1 | * | 12/2015 | Lytvynenko ........... G01N 22/00 73/31.06 |

OTHER PUBLICATIONS

James et al., "Chemical Sensors for Electronic Nose Systems", Microchm Acta 149, pp. 1-17, 2005.
Wagner T. et al., "A high-density . . . FPGA control", Procedia Chemistry, vol. 1, No. 1, Sep. 1, 2009, pp. 1483-1486.

* cited by examiner

METHOD AND DEVICE FOR CHARACTERISING A FLUID MEDIUM USING A PHOTOELECTRIC TRANSDUCER

The present invention relates to the technical field of recognizing or characterizing a fluid medium in the general sense, with the help of a photoelectric transducer.

There are numerous applications for identifying fluid media and/or products or substances contained in fluid media, such as for example detecting products or substances in a fluid medium, quality control, or compliance checking, etc.

In the state of the art, the publication "A high density multipoint LAPS setup using VCSEL array and FPGA control" Sensors and Actuators B154 (2011), pp. 124-128, discloses a sensor known by the acronym L.A.P.S. (for light-addressable potentiometer sensor), of structure that comprises a potentiometer transducer in contact with the liquids for analysis and separated from a semiconductor element by an insulator. A modulated light source is used to create localized photon excitation that penetrates directly into the interior of the semiconductor element in order to generate electron-hole pairs in said element. A bias voltage applied to the terminals of the sensor leads to a photocurrent being generated. The value of the photocurrent depends in particular on the bias voltage, on the photon excitation, and on the potential of the interface between the liquid and the insulator.

It stems from the principle on which that sensor is based that the photocurrent signal is of a photocapacitive nature because of the interface between the insulator and the semiconductor. As a result, the sensitivity of such a sensor is low and the detected signal is of low power. Furthermore, it is found that the zones that are not lighted have an influence on the signal created by the localized zones that are lighted.

Also known in the state of the art is the publication "Chemical sensors for electronic nose systems", Microchim. Act 1.49, pp. 1-17 (2005), which discloses an electronic nose system using a chemical sensor for analyzing volatile organic compounds. Such a system has a metal oxide semiconductor field effect transistor (MOSFET). The grid of the transistor is in contact with the gas for analysis and is separated from the drain-source junction by an insulator. Charges on the insulator influence the drain-source current by means of a field effect and consequently influence the photocurrent picked up across the terminals of the transistor, thus enabling the gas for analysis to be characterized.

It stems from the principle of that electronic nose that the current signal between the drain and the source is modulated by the field effect via the interface between the insulator and the fluid. A drawback of that electronic nose lies in the need to have a specific grid in order to characterize gases selectively. In this respect, and by way of example, in order to be sensitive to compounds that are neutral, it is necessary to use specific catalysts so as to decompose the neutral molecules into charged elements. Another drawback of that electronic nose (from the point of view of technologically implementing it) lies in the need for the drain and the source of each transistor to be electrically insulated from the fluid for analysis. The spatial resolution of that device is defined and limited by the size of each transistor.

A system for detecting hydrogen is also known from Document US 2006/0042354, which system comprises a semiconductor substrate having, on one side, a stack of layers including an electrically insulating layer, an ion-conductive layer, and a first conductive electrode. The other side of the semiconductor substrate is provided with a second conductive electrode. The semiconductor substrate is subjected to a pulsed laser beam, and the photocurrent that is generated is measured, thereby enabling the concentration of hydrogen to be determined. The photocurrent that is created possesses a capacitive nature because of the presence of an electrically insulating layer covering the entire semiconductor substrate. The lighting is applied to the side opposite from the interface between the substrate and hydrogen, so that only one value is measured for the interface that is created. Such a detection system does not make it possible to identify a given gas in an arbitrary mixture of gases.

The present invention seeks to remedy the drawbacks of the prior art by proposing a novel method using a photoelectric transducer to characterize a fluid medium, i.e. a liquid and/or a gas and/or products or substances contained in fluid media, which medium may optionally be electrically neutral, the characterization method presenting high sensitivity and spatial resolution that is easily adaptable.

In order to achieve such an object, the invention provides a method of characterizing a fluid medium with the help of a photoelectric transducer having at least one semiconductor substrate possessing at least one space charge zone.

According to the invention, the method comprises the following steps:
  making a reception surface for receiving the fluid medium on at least one face of the photoelectric transducer;
  putting the fluid medium for characterizing into contact with the reception surface so as to make an interface between the substrate and the fluid medium;
  lighting a plurality of zones of the interface successively in time through the fluid medium with the help of an amplitude-modulated light beam in order to create photogenerated electric charges;
  for each lighted zone of the interface, recovering the values of at least one photoelectric magnitude of value that depends on the lighting conditions and on the electronic properties of the interface between the substrate and the fluid medium;
  creating at least one one- or two-dimensional matrix of values of the recovered photoelectric magnitude; and
  from the matrix that has been created of values of the photoelectric magnitude, determining an electronic signature that is characteristic of the fluid medium.

In addition, the method of the invention may also present in combination at least one or more of the following additional characteristics:
  characterizing the fluid medium with the help of a photoelectric transducer in which the semiconductor substrate possesses at least one space charge zone that is specially created in the semiconductor substrate from a diode type junction:
    by creating photogenerated electric charges that diffuse towards the diode type junction on lighting through the fluid medium;
    by recovering the photocurrents passing through the diode type junction and obtained from photogenerated electric charges of quantity that is determined by the rate of recombination at the interface between the substrate and the fluid medium;
    by creating a matrix of recovered photocurrent values; and
    by determining the electronic signature characteristic of the fluid medium from the created matrix of photocurrents;
  characterizing the fluid medium with the help of a photoelectric transducer in which the semiconductor substrate presents a space charge zone that exists naturally at the surface of the semiconductor at the interface between the substrate and the fluid medium, the substrate being provided with a first electrode in contact with the fluid medium and with a second electrode providing electrical contact with the face of the substrate that is opposite from the interface:
- by recovering the photovoltage by performing capacitive measurements with the help of the first and second electrodes;
- by creating a matrix of recovered photovoltage values; and
- by determining the electronic signature characteristic of the fluid medium from the created matrix of photovoltages;

renewing the steps of lighting, of recovering the photoelectric magnitude, of creating the matrix, and of determining the electronic signature by modifying one and/or more of the following parameters: the application time of the lighting; the intensity of the lighting; the area of the lighting; the wavelength of the lighting; the temperature of the fluid medium and/or of the transducer; and applying an additional electric voltage to the transducer;

determining at least one visual image of the values of the photoelectric magnitudes as an electronic signature characteristic of the fluid medium;

subdividing the field over which the photoelectric magnitude varies into areas, with a color being allocated to each of them so that the electronic signature is a color image;

lighting the interface zone with light flux coming either from a single light beam that moves relative to the transducer in discrete or continuous manner, or else from at least one LED forming part of an array of LED that are selectively switched on and off;

performing a step of analyzing the electronic signature in order to recognize the fluid medium and/or one or more of its individual components;

comparing the electronic signature of the fluid medium with at least one reference electronic signature determined for a known fluid medium;

using quantitative methods of processing the images obtained; and performing a processing step on the reception surface prior to performing the lightning step.

Another object of the invention is to provide a device for characterizing a fluid medium with the help of a photoelectric transducer.

According to the invention, the device comprises:
- at least one semiconductor substrate possessing at least one space charge zone and presenting a reception surface for receiving the fluid medium in order to constitute an interface between the substrate and the fluid medium;
- a production system for producing a spot light beam that is amplitude-modulated and that lights at least one zone of the interface through the fluid medium;
- a system for controlling the spot light beam so as to light a plurality of zones of the interface in succession;
- a measurement system for measuring values of a photoelectric magnitude delivered while performing the lighting each zone of the interface so as to create a one- or two-dimensional matrix of values of the photoelectric magnitude; and
- a processor system for processing values of the photoelectric magnitude delivered by the measurement system and adapted, on the basis of the matrix, to determine an electronic signature characteristic of the fluid medium.

Furthermore, the device of the invention may also include in combination at least one and/or more of the following additional characteristics:
- the production system for producing a spot light beam comprises either a spot light source optionally associated with a system for moving the system for producing the spot light beam, or else an array of LEDs each subjected to on/off control;
- the measurement system for measuring the values of the photoelectric magnitude includes an external recovery circuit comprising:
  - either a first electrode placed on the face of the semiconductor substrate forming the interface and a second electrode placed on the opposite face of the semiconductor substrate;
  - or a first electrode and a second electrode placed on the face of the semiconductor substrate opposite from the face forming the interface;
  - or else an optically transparent first electrode in contact with the fluid medium on one side and in contact on its opposite side with an optically transparent protective plate, and a second electrode placed on the face of the semiconductor substrate that is opposite from the face forming the interface;
- the measurement system also includes an optically transparent electrode in contact with the fluid medium and serving to apply a voltage between said electrode and an electrode placed on the face of the semiconductor substrate opposite from its face forming the interface so as to create matrices of photocurrent values for different values of the voltage applied between the electrodes;
- the measurement electrodes provided on the face of the semiconductor substrate opposite from its face forming the interface are made in the form of interleaved combs; and
- the simultaneous measurements are performed between the electrodes in order to make up pluri-dimensional matrices in order to establish a characteristic electronic signature of the fluid medium.

Various other characteristics appear from the following description made with reference to the accompanying drawings, which show embodiments of the invention as non-limiting examples.

FIG. 1 is an elevation view in section shown the general principle of the invention.

FIGS. 2A, 2B, and 2C show examples of images obtained using matrices of values as measured respectively with air, water, and alcohol as the fluid medium.

FIG. 3 shows a first embodiment of the device of the invention in which a p-n junction of diode type is specially created in the semiconductor substrate, and the measured photoelectric magnitude is a photocurrent, for example.

FIGS. 3A, 3B, and 3C show the mechanism whereby the photocurrent appears in the embodiment shown in FIG. 3.

FIGS. 4 and 4A show a variant of this first embodiment of FIG. 3, making use of a chemical treatment layer.

FIGS. 5, 5A, and 5B are respectively views from above, in section, and from below showing a variant of this first embodiment in which the electrodes are made on the face of the semiconductor substrate opposite from its face that receives the liquid medium.

Figure 1:
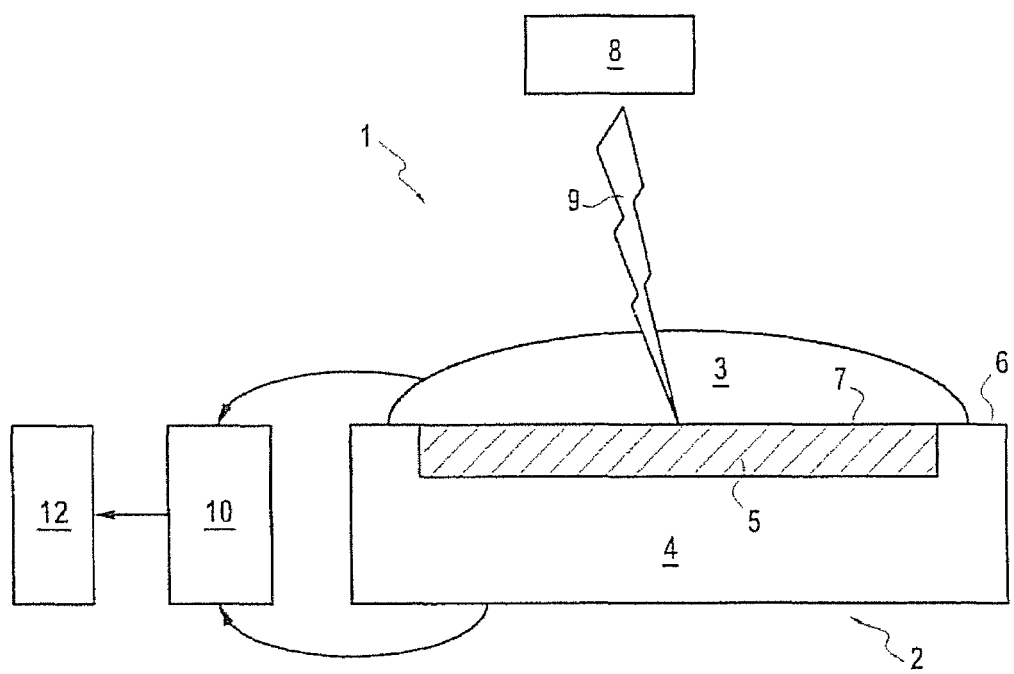

FIG. 1 shows the principle of a device 1 in accordance with the invention suitable for characterizing a fluid medium 3 in the general sense with the help of a photoelectric transducer 2. In the meaning of the invention, a fluid medium is a liquid, a gas, or a gaseous liquid, of homogeneous or heterogeneous nature, i.e. containing various substances, products, or compounds such as, by way of example: biological objects (bacteria, cells, viruses, proteins, etc.) or particles in the solid state that may be suspended or dissolved in the liquid media or evaporated in the form of a gas. The term "characterizing" is thus used for the fluid medium to mean identifying at least one specific compound forming the fluid medium or contained in the fluid medium. As non-limiting examples, it is possible to use as the fluid medium food industry products, cosmetics, fragrances, biomedical products, hydrocarbons, drugs, explosive substances, . . . .

The photoelectric transducer 2 comprises at least one semiconductor substrate 4 possessing at least one space charge zone 5 that exists naturally or that is specially created. The semiconductor substrate 4 has a reception surface 6 for the fluid medium 3 in order to constitute an interface 7 between the substrate 4 and the fluid medium 3. By way of example, the semiconductor substrate 4 is constituted by a standard silicon substrate of microelectronic quality without any special treatment. For example, the reception surface 6 of the semiconductor substrate 4 may be naturally oxidized in air.

The device 1 of the invention also has a production system 8 for producing an amplitude-modulated spot light beam 9 and adapted to light at least one zone of the interface 7 through the fluid medium 3. The production system 8 is controlled to light a zone of the interface 7 for a determined duration. The production system 8 is adapted to illuminate one or more zones of the interface 7 after passing through the fluid medium 3 by using an amplitude-modulated light beam.

The production system 8 is made in any appropriate manner and may, by way of example, comprise a point light source or an array of light-emitting diodes (LEDs) with on/off control.

The device 1 has a system for controlling the spot light beam so as to light successively a plurality of zones of the interface. In particular, the system for controlling the spot light beam has a system for moving the system for producing the spot light beam so as to be capable of illuminating different zones of the interface 7.

In another variant embodiment, the production system 8 has an array of LEDs distributed spatially and subjected to selective on/off control so as to light a plurality of different zones of the interface 7.

The device 1 of the invention also has a measurement system 10 for measuring values of a photoelectric magnitude delivered during lighting in order to create a matrix of values of the photoelectric magnitude. As explained in greater detail in the description, the photoelectric transducer 2 serves, while the interface 7 is being illuminated, to generate a photoelectric magnitude that is either a photocurrent or a photovoltage. The system 10 thus acts on each occasion the interface zone 7 is lighted to measure the value of the photoelectric magnitude. This value of the photoelectric magnitude depends on lighting conditions (i.e. and by way of on the duration of lighting, on the brightness, on the wavelength, and on the frequency at which the light source is modulated and the size of the interface zone 7) and also on the electronic properties of the interface 7 (i.e., and by way of example, on the concentration and the nature of dopants in the semiconductor substrate 4, on the energy of the forbidden bands, on the curvature of the electron bands of the semiconductor substrate 4 at the interface 7, on the potential of the flat bands of the semiconductor substrate 4, and on the rate of recombination of the charge carriers that are photogenerated at the interface 7).

In a preferred variant, the system 10 also records the measured values of the photoelectric magnitude in order to create a matrix of values corresponding to the values of the photoelectric magnitude as measured in different zones of the interface 7 that are illuminated successively in time. For this purpose, the measurement system 10 includes storage means of any known type.

The dimension of this matrix of values depends on the number of illuminated zones and/or on the number of external parameters that are defined and controlled while taking the measurements, such as for example: time, temperature, lighting conditions, electric field, etc. By way of example, when lighting a single zone while keeping the external measurement parameters constant, the matrix has only one value. When lighting n interface zones 7 distributed along a direction of the interface 7 and when keeping the external measurement parameters constant, a one-dimensional matrix is obtained. When successively lighting n interface zones 7 that are distributed in rows and columns (where n is greater than 1) and when keeping external measurement parameters constant, the matrix of n values has two dimensions.

The device 1 of the invention also has a processor system 12 for processing values of the photoelectric magnitude delivered by the measurement system 10 and adapted to use the matrix to determine a fingerprint or an electronic signature that is characteristic of the fluid medium. In other words, the processor system 12 serves to characterize the fluid medium from the measured values of the photoelectric magnitude.

The processor system 12 uses various methods for characterizing the fluid medium from the measured values of the photoelectric magnitude. A simplified method consists in characterizing the fluid medium directly from the measured values of the photoelectric magnitude. In an advantageous variant, the measured values of the photoelectric magnitude are represented in the form of an image. In this variant, the matrix of values of the photoelectric magnitude is converted into or represented in the form of a visual image having one or more colors, possibly also with one or more shades of the colors. Thus, the field over which the values of the photoelectric magnitude vary is subdivided into a plurality of areas with a color or a color shade being allocated to each of them so that a two-dimensional matrix of values gives rise to a corresponding color image that is likewise in two dimensions.

Figure 2A:
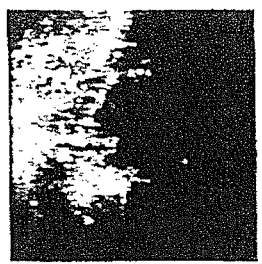
Figure 2B:
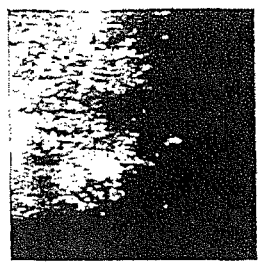
Figure 2C:
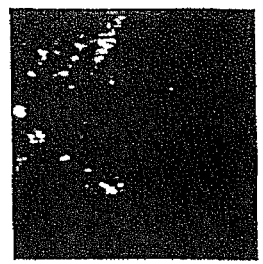

FIG. 2A shows an example of an image obtained from a matrix of values of the photoelectric magnitude, as measured in air as the fluid medium. The paler zones of the image correspond to greater values in the matrix. FIGS. 2B and 2C give examples of images obtained with matrices of values as measured respectively in water and in alcohol as the fluid medium.

The description below gives other examples for illustrating the subject matter of the invention, which is implemented in essentially two embodiments.

Figure 3:
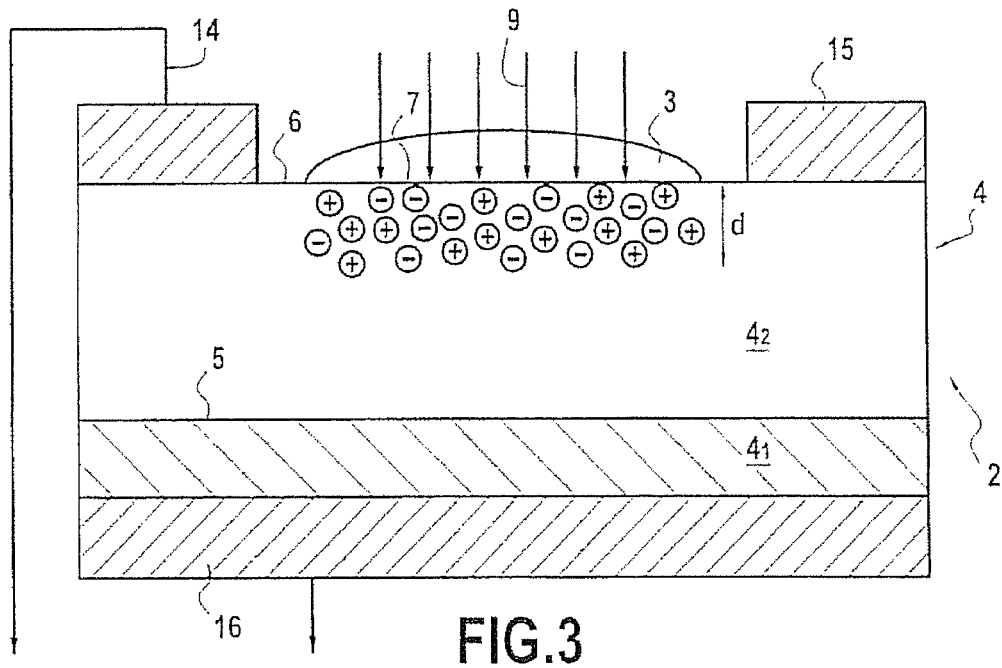

FIG. 3 shows a first embodiment of a photoelectric transducer 2 in which the semiconductor substrate $4_1$, $4_2$ possesses at least one space charge zone 5 made by a diode type junction. In the example shown in FIG. 3, the space charge zone 5 is made by a p-n junction. For this purpose, the semiconductor substrate 4 possesses by way of example a layer $4_1$ of n-type silicon in contact with a layer $4_2$ of p-type silicon. In this first embodiment, the measured photoelectric magnitude is a photocurrent, for example.

FIGS. 3, 3A, 3B, and 3C serve to illustrate the mechanism whereby a photocurrent appears as a result of photogenerated electric charges being created.

As shown in FIG. 3, a fluid medium is put into contact with the surface 6 of the semiconductor substrate and more precisely with the layer $4_2$ of p-type silicon so as to obtain the interface 7 between the substrate and the fluid medium. Lighting a zone of the interface 7 through the fluid medium 3 for a determined length of time leads to electric charges (electrons $e^-$ and holes$^+$) being created inside the layer $4_2$ of p-type silicon starting from the interface 7. It should be observed that the depth of generation d depends in particular on the wavelength of the light beam 9 and on the physicochemical nature of the semiconductor layer $4_2$.

Figure 3A:
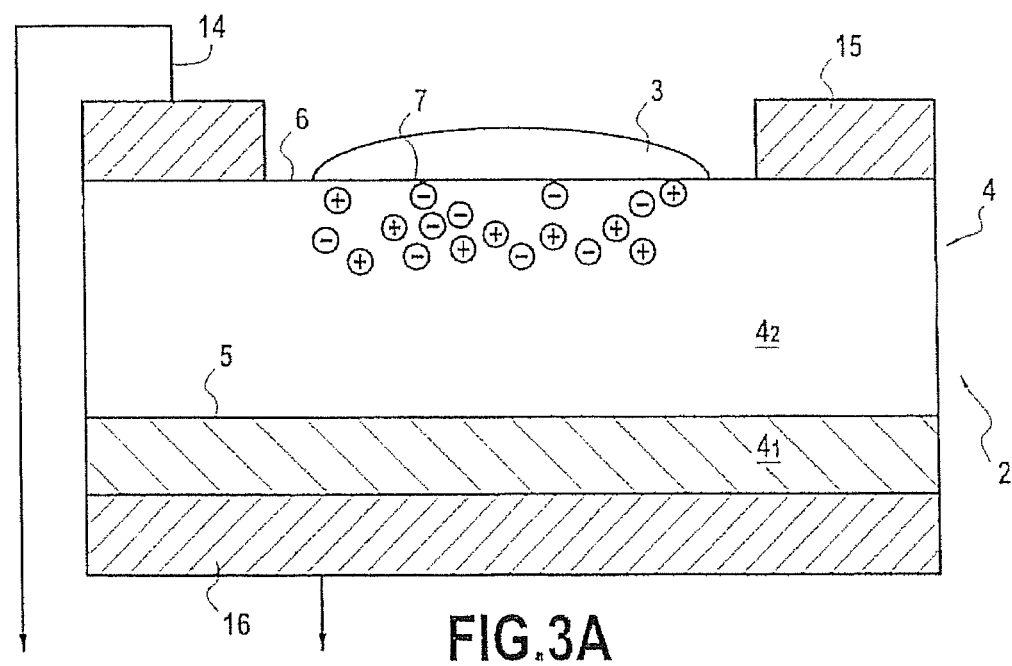

After electric charges have appeared within the layer $4_2$ of p-type silicon, some of these photogenerated electric charges inevitably recombine, as shown in FIG. 3A. This recombination is a function of the electronic nature and the quality of the reception surface 6. This recombination of some of the photogenerated electric charges is characterized by its rate of recombination.

Figure 3B:
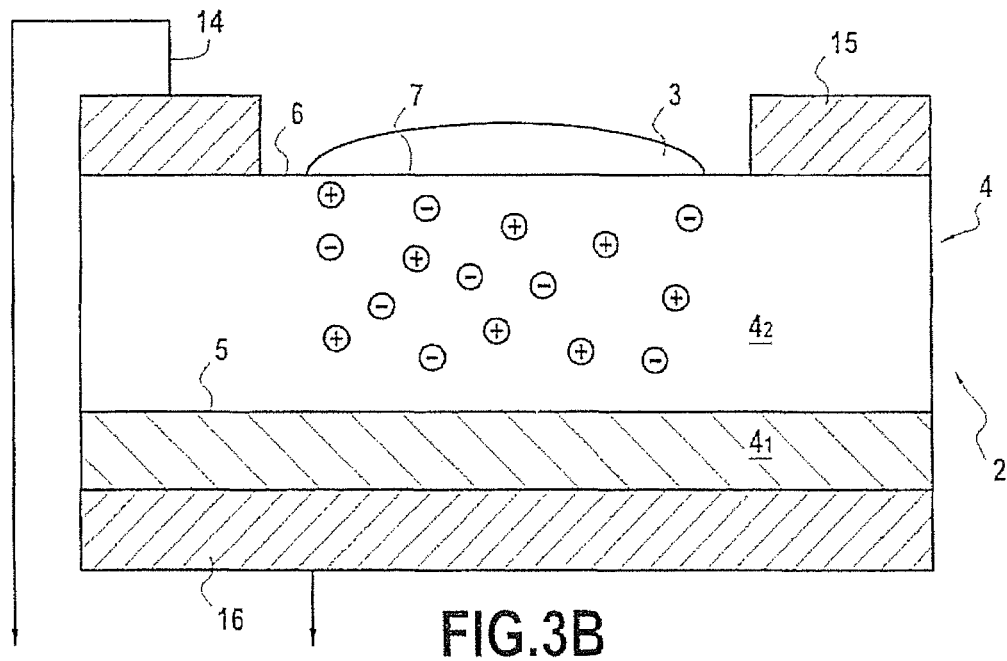

The non-recombined photogenerated electric charges diffuse within the layer $4_2$ of p-type silicon during their lifetimes (FIG. 3B). The lifetimes of the non-recombined photogenerated electric charges depend on the electronic nature and the quality of the layer $4_2$ of p-type silicon.

Figure 3C:
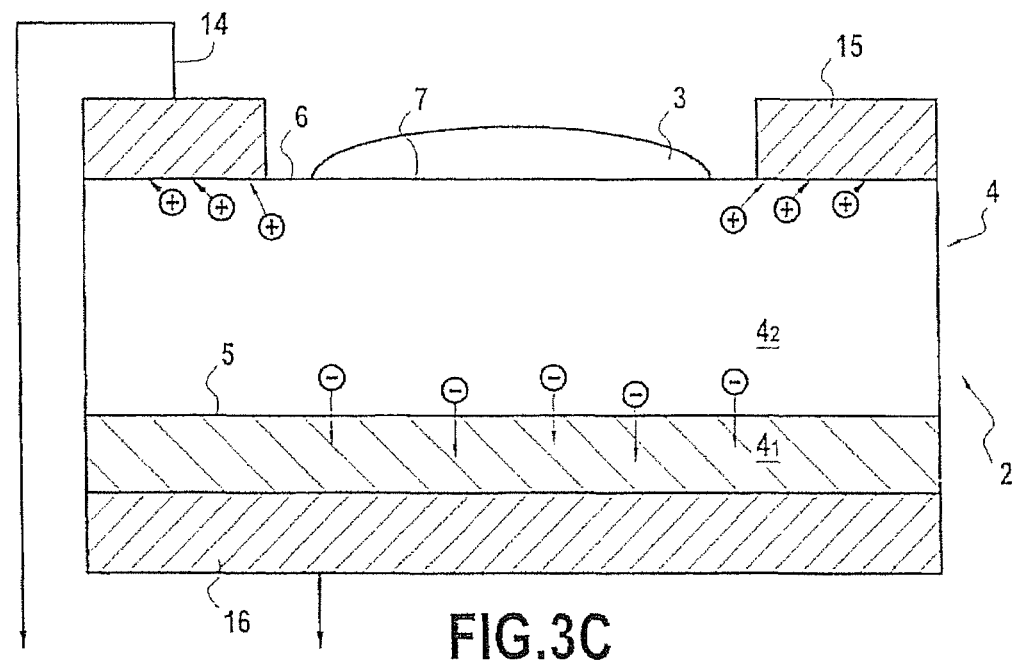

The photogenerated electric charges that diffuse within the layer $4_2$ of p-type silicon are then separated by the field of the p-n junction so as to be recovered by an external recovery circuit 14 forming part of the measurement system 10 (FIG. 3C). The external recovery circuit 14 serves to pick up the photocurrents passing through the diode type junction and obtained from the photogenerated electric charges in a quantity that is determined by the rate of recombination at the interface 7 between the substrate and the fluid medium.

It can be seen from the above-described principle that the measured value of the photocurrent after lighting the interface 7 is defined directly by the recombination rate of the photogenerated electric charges. There thus exists a direct and unique correlation between the characteristics of the lighted zone of the interface 7 and the value of the photocurrent as measured with the external circuit 14. It is possible to obtain high measurement sensitivity over a wide range of values for measured photocurrents insofar as the recombination rate can vary over several orders of magnitude (e.g. in the range $10^2$ centimeters per second (cm/s) to $10^6$ cm/s).

The spatial resolution of the measurement, which is responsible for the quality of the recognition or of the characterization of the fluid medium and which defines the minimum area value for the reception surface 6, depends on the size of the light spot, i.e. on the area of the lighted zone of the interface 7. The spatial resolution of the measurement also depends on the minimum movement of the light spot for which it is possible to detect a change in photocurrent. In other words, the spatial resolution depends on the degree of heterogeneity in the rate of recombination at the reception surface 6.

In an aspect of the invention, it is found advantageous to characterize a fluid medium by successively lighting a plurality of different zones of the interface 7 that present different rates of recombination, either naturally or as a result of special treatment. Specifically, it has been observed that the interface 7 naturally presents different rates of recombination that are spread over the surface of the interface 7. Of course, it is possible to envisage applying treatment, e.g. chemical treatments, to the reception surface 6 in order to obtain different recombination rates that are selectively distributed over the reception surface 6. By way of example, it is possible to envisage the following treatments for chemically treating the reception surface of the substrate:
  oxidizing, nitriding, carbonizing, or porosification of the initial substrate;
  depositing layers of oxides, nitrides, carbides, or various porous layers on the surface of the substrate;
  chemically grafting organic functional groups by hydrosilylation (e.g. a fresh Si surface);
  chemically grafting organic functional groups by silanization (e.g. an oxidized or nitrided Si surface);
  electrochemically grafting organic functional groups;
  grafting organic functional groups with alcohols or amines;
  consecutive reconstructions of the surface of the substrate with organic functional groups;
  filling pores of porous layers formed with polymers, nanoparticles (carbon, semiconductor, or metal nanoparticles), or water-insoluble weakly-polar liquids; and
  within the pores or on the surface of the substrate, growing layers or membranes that are sensitive to the ions and ionophoric solutions in the polymers.

The presence of different recombination rates at the interface 7 makes it possible to create a matrix of photocurrent values recovered by the external circuit 14.

In the example shown in FIG. 3, the external circuit 14 has a first electrode 15 situated on the face of the semiconductor substrate that forms the interface 7 and a second electrode 16 made on the face of the semiconductor substrate that is opposite from the face forming the interface 7. In other words, the first electrode 15 is situated on the face of the semiconductor substrate that receives the fluid medium 3. These first and second electrically conductive electrodes 15 and 16 are made using conventional microelectronic techniques.

Figure 4:
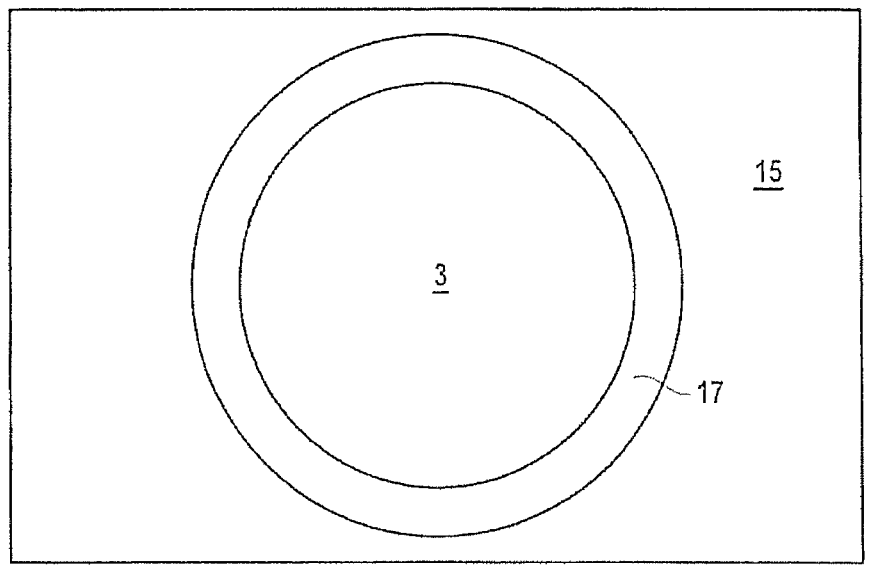
Figure 4A:
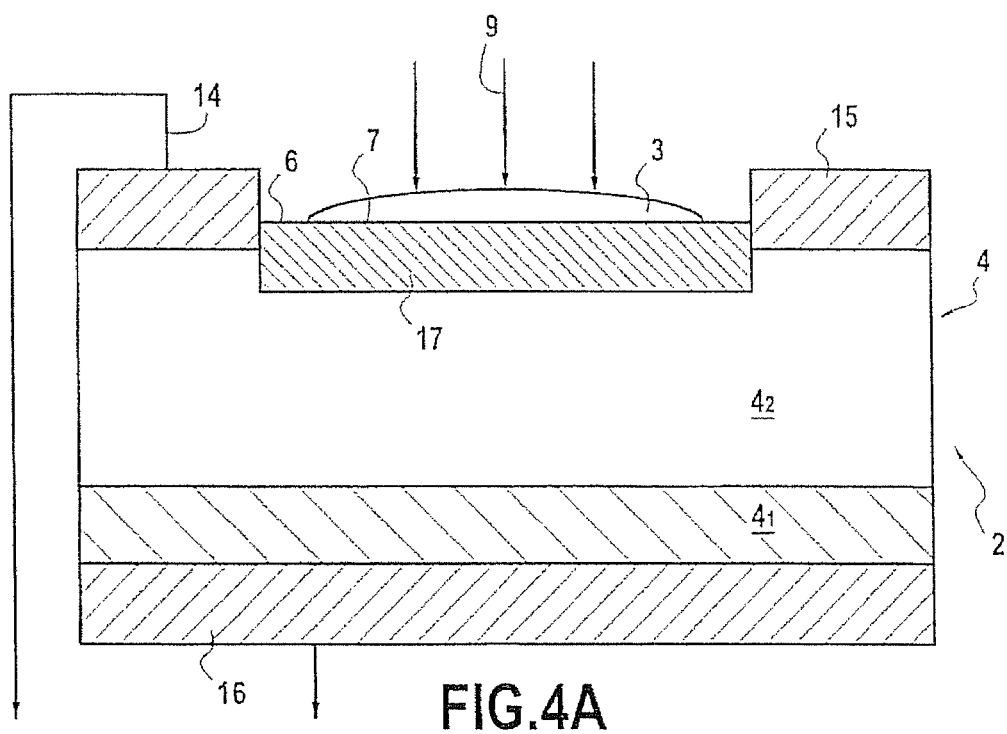

FIGS. 4 and 4A show a variant of this first embodiment in which the first electrode 15 surrounds the reception surface 6 for receiving the fluid medium that corresponds to the top surface of a layer 17 of chemical treatment performed in the layer $4_2$ of p-type silicon. As explained above, such chemical treatment for making the layer 17 that receives the fluid medium 3 makes it possible to obtain recombination rates that are different and that are distributed heterogeneously over the reception surface 6.

Figure 5:
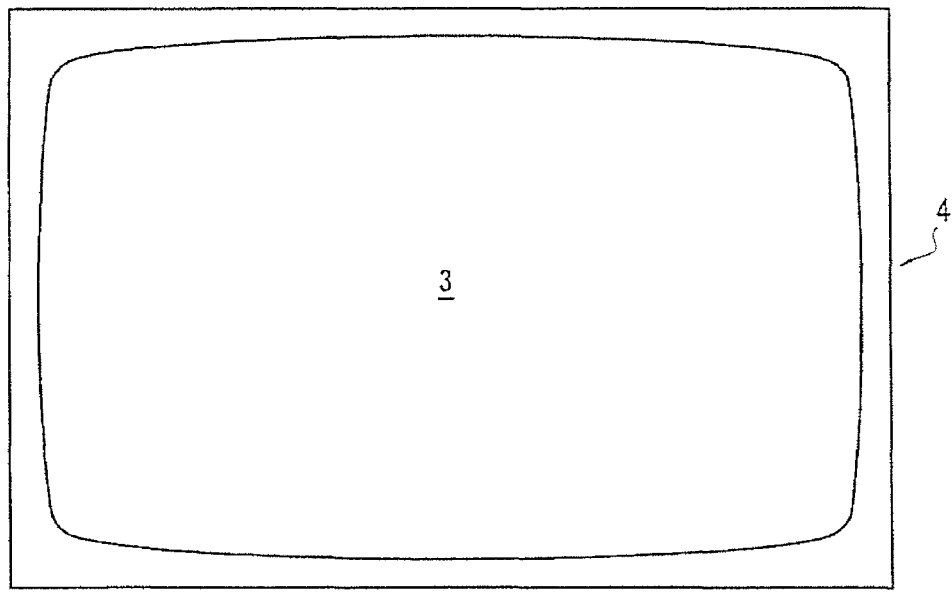
Figure 5A:
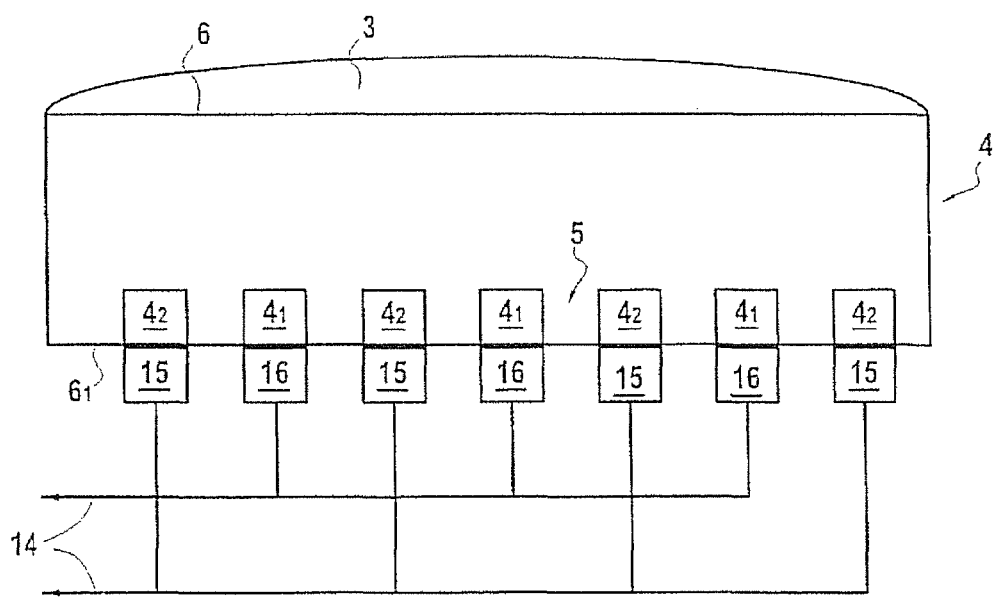
Figure 5B:
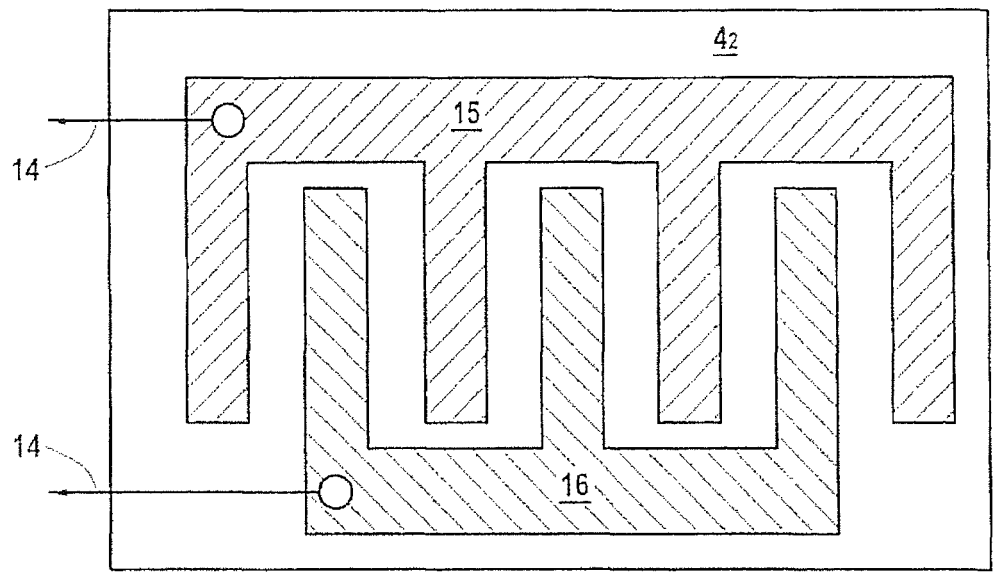

FIGS. 5, 5A, and 5B show a variant of this first embodiment in which the first and second electrodes 15 and 16 of the external circuit 14 are made on the face of the semiconductor substrate that is opposite from its face forming the interface 7. In this variant, the photoelectric transducer 2 comprises a p-type silicon semiconductor substrate 4 having its top face 6 forming the reception surface for receiving the fluid medium. The semiconductor substrate possesses a space charge zone 5 made as a p-n type diode junction starting from the bottom face $6_1$ of the semiconductor substrate. For this purpose, the p-type silicon semiconductor substrate 4, possesses, going from its bottom face $6_1$, and by way of example: a layer $4_1$ of n-type silicon separated from a layer $4_2$ of $p^+$-type silicon. In the embodiment shown more particularly in FIG. 5B, the layers $4_1$ and $4_2$ are made in the form of interleaved combs.

The layer $4_1$ of n-type silicon and the layer $4_2$ of $p^+$-type silicon are in contact respectively with first and second electrically conductive electrodes 15 and 16 forming part of the external circuit 14. The external circuit 14 recovers the photocurrent generated by the above-explained principle.

Figure 6:
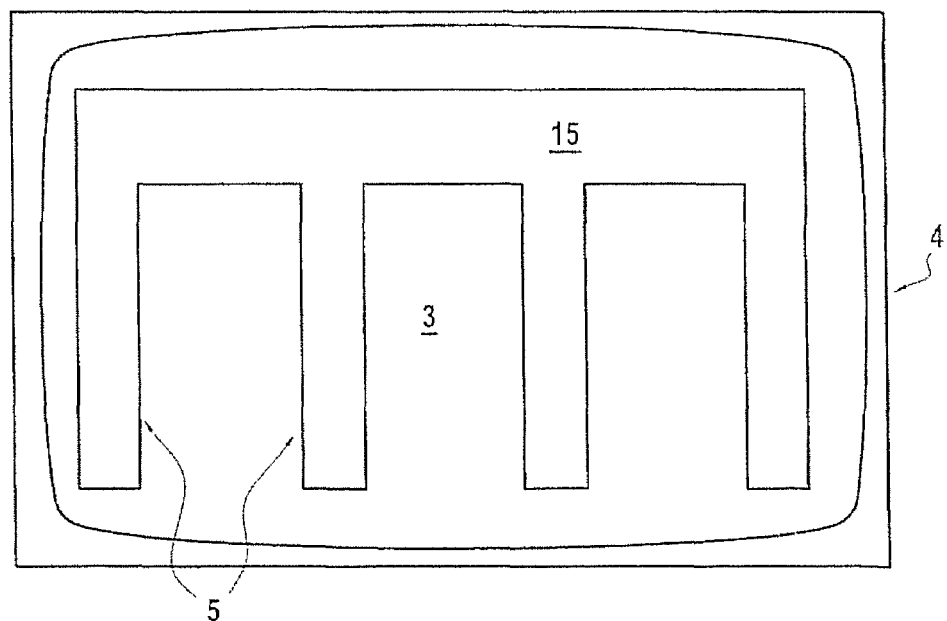
FIGS. 6 and 6A are respectively views from above and in section showing another variant of the first embodiment in which the semiconductor substrate possesses a diode junction of metal-semiconductor type that is created in the semiconductor substrate.
Figure 6A:
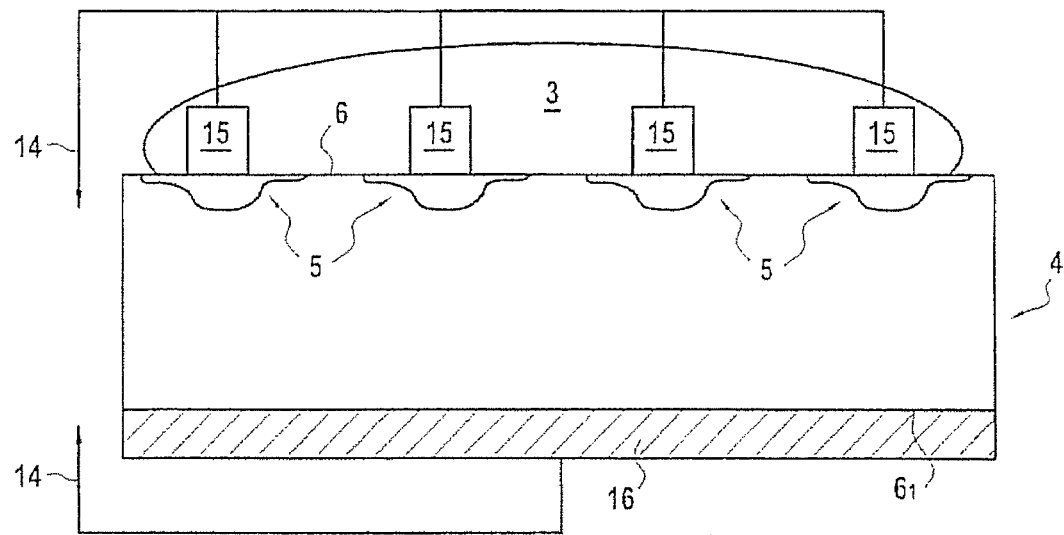

FIGS. 6 and 6A show another variant of this first embodiment in which the semiconductor substrate 4 possesses a space charge zone 5 in the form of a metal-semiconductor diode junction. In this variant, the photoelectric transducer 2 has a p-type semiconductor substrate with its top face 6 forming the reception surface for receiving the fluid medium 3. The semiconductor substrate 4 possesses a space charge zone 5 made as a metal-semiconductor or Schottky contact type diode junction. As can be seen in FIGS. 6 and 6A, a layer 15 of an electrically conductive material is locally deposited on the top face 6 so as to form a space charge zone 5 facing the inside of the semiconductor substrate 4 and starting from the top face 6. In the example shown, the layer of electrically conductive material 15 is deposited so as to present a comb shape with its various portions in contact with the fluid medium.

The layer of the electrically conductive material 15 forms the first electrode of the external circuit 14, while the second electrode 16 is made as a layer of electrically conductive material deposited on the bottom face $6_1$ of the semiconductor substrate. The external circuit 14 recovers the photocurrent generated on the above-explained principle.

The above-described variant embodiments rely on using diode type junctions specially created in the semiconductor substrate 4 and they make it possible to create photogenerated electric charges that lead to photocurrents being recovered using the external circuit 14. It is then possible to create a matrix of photocurrents in order to determine the electronic signature of the fluid medium.

Figure 7:
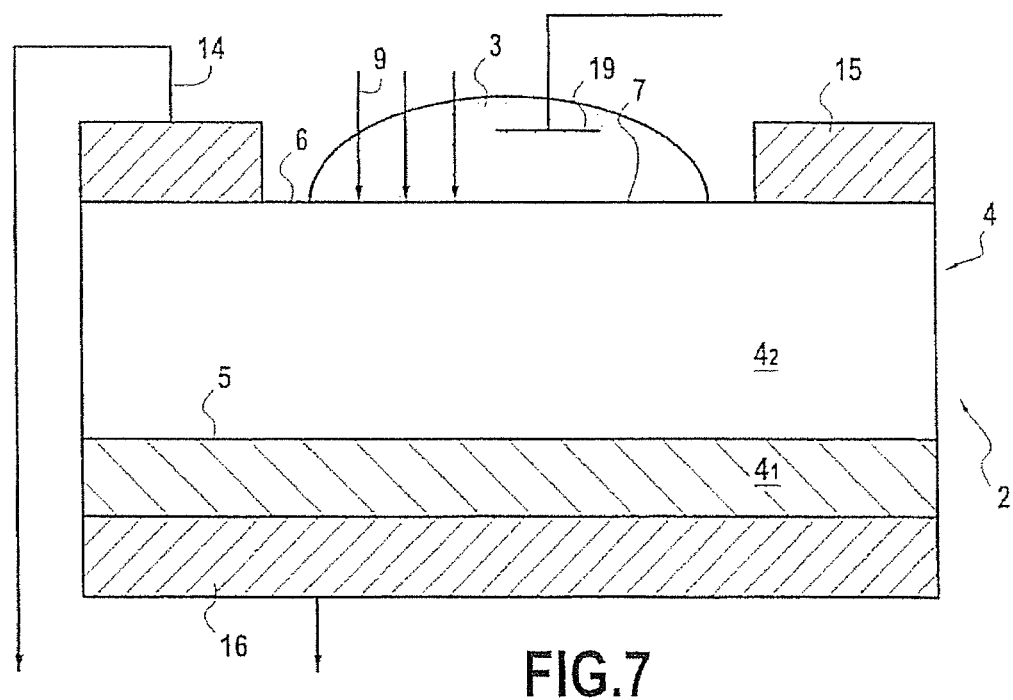
FIG. 7 shows an example of a variant making use of a voltage biasing the fluid medium.

In a variant, provision is made to create photocurrent matrices for different values of a bias voltage applied to the fluid medium. FIG. 7 shows an example of this variant for the transducer embodiment shown in FIG. 3. Naturally, this variant may be applied to any one of the variants shown in FIGS. 4 to 6. As can be seen in FIG. 7, a first bias electrode 19 is placed in contact with the fluid medium 3. This bias electrode 19 lies outside the light flux 9 or it is made of a material that is optically transparent and that is arranged on an optically transparent plate in contact with the fluid medium. The bias voltage is applied between this first bias electrode 19 and a second bias electrode that is applied against or advantageously constituted by the first or the second electrode 15, 16 of the external circuit 14.

A bias voltage at a determined value is applied while lighting a plurality of zones of interface 7 that are involved successively in time to enable photocurrents to be recovered and a matrix of photocurrents to be created. The value of the bias voltage is changed and a new sequence of lighting the interface 7 makes it possible to recover photocurrents and to create a new matrix of photocurrents obtained with a different bias voltage. Making a plurality of two-dimensional matrices of photocurrents with different bias voltages serves to significantly improve the quality with which the fluid medium is recognized or characterized.

Figure 8:
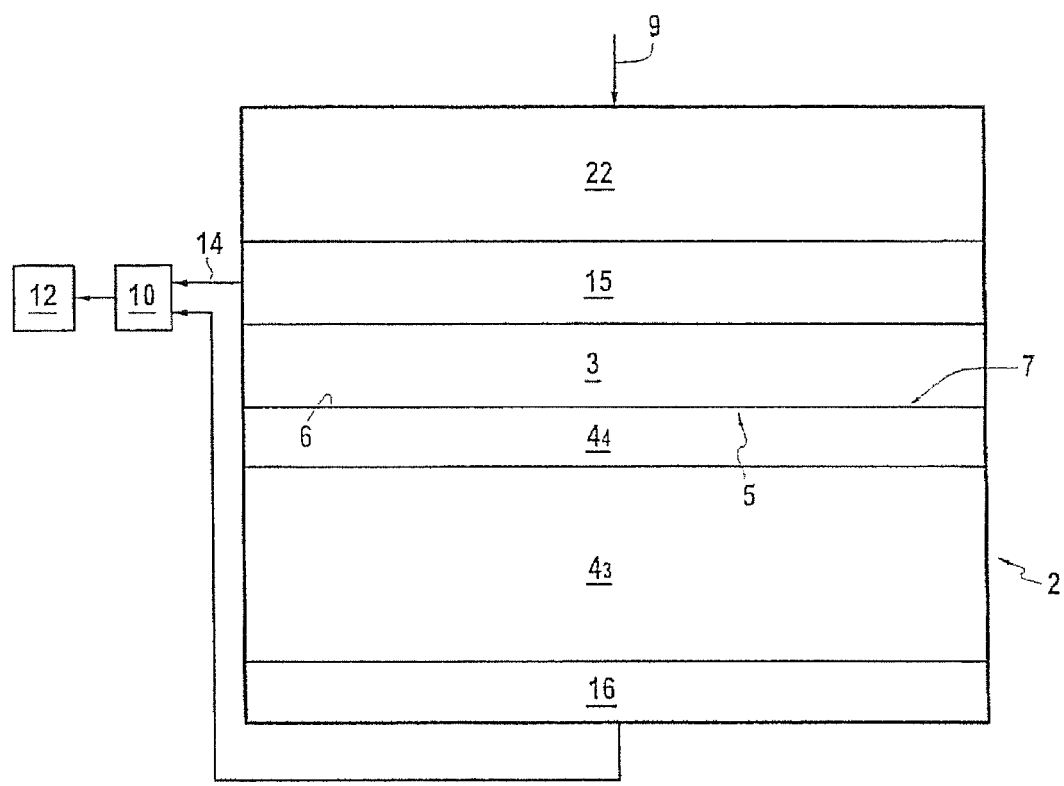
FIG. 8 shows a second embodiment of the device of the invention in which use is made of the space charge zone that exists naturally at the surface of the semiconductor, and the measured photoelectric magnitude is a photovoltage, for example.

FIG. 8 shows a second embodiment of the device of the invention in which use is made of the space charge zone 5 that exists naturally at the surface of the semiconductor, and by way of example the measured photoelectric magnitude may be a photovoltage. In this second embodiment, the photoelectric transducer 2 comprises a semiconductor substrate $4_3$ possessing at least one space charge zone 5 existing at the interface 7 between the substrate and the fluid medium 3. For this purpose, the semiconductor substrate $4_3$ may possess a surface layer $4_4$ having its top portion serving as the reception surface 6 for receiving the fluid medium 3. By way of example, the surface layer $4_4$ may be made by a porous layer of silicon or by any other chemically active layer. The fluid medium 3 is in contact with a first electrode 15 that is optically transparent and suitable for passing the light beam. This first electrode 15 is covered by an optically transparent protective plate 22. This first electrode 15 forms part of the circuit 14 for recovering the photovoltage that includes a second electrode 16 in electrical contact with the face of the semiconductor substrate $4_3$ that is opposite from the interface 7.

When the zone of the interface 7 is lighted through the fluid medium, photogenerated electric charges appear in the semiconductor substrate $4_3$ and they are immediately separated by the electric field existing in the space charge zone 5 that exists naturally at the surface of the semiconductor, thereby leading to a photovoltage appearing that is measured by using the first and second electrodes 15 and 16 of the recovery circuit 14. As explained above, the measurement circuit 10 makes it possible to create a matrix of photovoltage values recovered during the lighting of different zones of the interface 7. The processor system 12 enables the fluid medium 3 to be characterized on the basis of the measured photovoltage value.

It can be seen from the above description that the device 1 of the invention makes it possible to characterize or identify a fluid medium on the basis of the measured values of the photoelectric magnitude (photocurrent or photovoltage), which values are characteristic of said fluid medium.

It should be observed that in an advantageous variant, the measurement system 10 performs measurements simultaneously both of photocurrent and of photovoltage values between the electrodes in order to make up pluri-dimensional matrices for establishing an electronic signature characteristic of the fluid medium. The method of identifying a fluid medium stems directly from the above description.

The method of the invention thus consists in:
  making a reception surface 6 for the fluid medium 3 on at least one face of the photoelectric transducer 2 that possesses at least one space charge zone 5;
  putting the fluid medium 3 for characterizing into contact with the reception surface 6 in order to make an interface 7 between the substrate and the fluid medium;
  lighting a plurality of zones of the interface 7 successively in time through the fluid medium with the help of an amplitude-modulated light beam so as to create photogenerated electric charges;

during the lighting sequence of lighting a plurality of zones of the interface 7 successively in time, recovering the values of at least one photoelectric magnitude of value that is dependent on the lighting conditions and on the electronic properties of the interface 7 between the substrate and the fluid medium;

creating at least one one- or two-dimensional matrix of values for the recovered photoelectric magnitude; and from the matrix that has been created of photoelectric magnitude values, determining an electronic signature characteristic of the fluid medium.

It should be understood that the method of the invention serves to identify a fluid medium from the matrix of recovered photoelectric magnitude values that forms a unique electronic signature for each fluid medium. Naturally, in order to increase the quality of detection, the detection method consists in renewing the steps of lighting, of recovering the photoelectric magnitude, of creating the matrix, and of determining the electronic signature, either while maintaining various experimental parameters constant or while modifying one and/or more of the following parameters, for example: lighting application time, lighting intensity, lighting area, lighting wavelength, temperature of the fluid medium and/or of the transducer, and applying an additional electric voltage to the transducer.

This electronic signature is preferably converted into a visual image. The fluid medium can be identified from one or more images using the naked eye, by comparison with a reference electronic signature determined for a known fluid medium, or with the help of various kinds of image processing, and in particular by using quantitative methods for processing the resulting images.

Figure 9A:
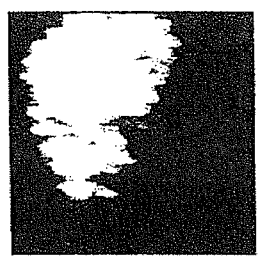
FIGS. 9A to 9C are images obtained three times over for the same fluid medium, namely isopropanol, and characterized using the method in accordance with the invention.
Figure 9B:
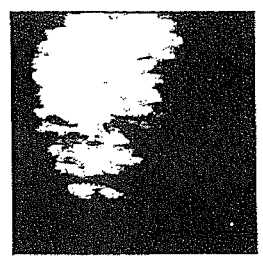
Figure 9C:
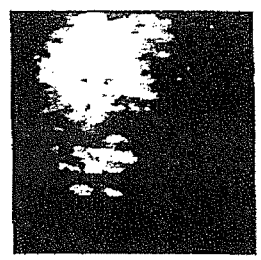

FIGS. 9A to 9C show the reproducibility quality of the measurements obtained by the invention. FIGS. 9A to 9C show examples of images obtained when repeating the method of the invention in order to characterize a fluid medium, specifically isopropanol in the example described. The three images obtained as a result of three measurements for characterizing isopropanol in accordance with the above-described technique presents similarities showing that the measurements performed have good reproducibility.

Figure 10A:
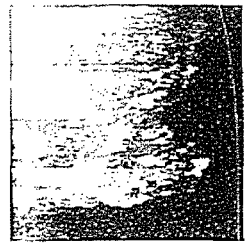
FIGS. 10A to 10C are images of three different samples of cognac, obtained using the method in accordance with the invention.
Figure 10B:
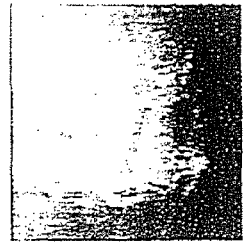
Figure 10C:
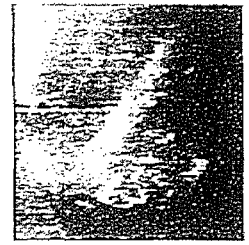

FIGS. 10A to 10C show images of a fluid medium, specifically cognac, all belonging to the same class, but coming from three different trademarks. In these images, it is possible to see the signatures that are specific to liquid products of the same category but that differ in terms of taste. A correlation between the images and taste can be established by analyzing the images.

Figure 11:
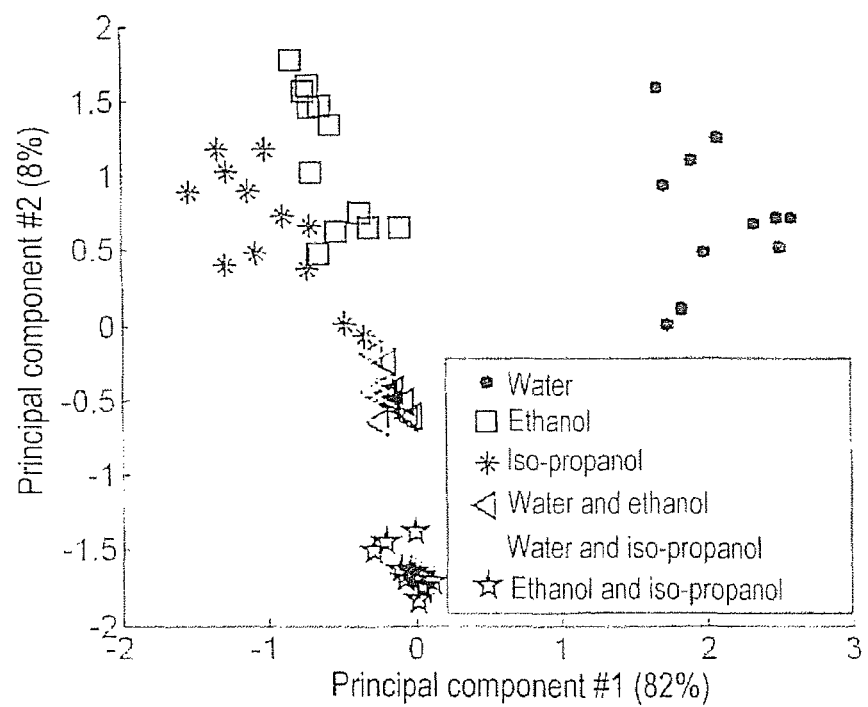
FIG. 11 shows an example of recognizing liquids as obtained with the principle components method.

In order to enable images to be recognized rigorously and in particular quantitatively, the method of the invention may be implemented using a specific mathematical protocol known in the literature as the method of principle components. FIG. 11 shows an example of such analysis performed for different liquids and mixtures thereof (water, ethanol, isopropanol). The greater the difference between the liquids, the more the points that correspond to them are spaced apart. It should be observed that even for mixtures that are very similar, it is possible to recognize clearly distinct spaces where points cluster.

The invention is not limited to the examples described and shown since various modifications may be applied thereto without going beyond its ambit.

The invention claimed is:

1. A method of characterizing a fluid medium (3) with the help of a photoelectric transducer (2) having at least one semiconductor substrate (4) possessing at least one space charge zone (5), the method being characterized in that it comprises the following steps:

making a reception surface (6) for receiving the fluid medium (3) on at least one face of the photoelectric transducer (2);

putting the fluid medium for characterizing into contact with the reception surface (6) so as to make an interface (7) between the substrate and the fluid medium;

lighting a plurality of zones of the interface (7) successively in time through the fluid medium (3) with the help of an amplitude-modulated light beam (9) in order to create photogenerated electric charges;

for each lighted zone of the interface (7), recovering the values of at least one photoelectric magnitude of value that depends on the lighting conditions and on the electronic properties of the interface (7) between the substrate and the fluid medium;

creating at least one one- or two-dimensional matrix of values of the recovered photoelectric magnitude; and from the matrix that has been created of values of the photoelectric magnitude, determining an electronic signature that is characteristic of the fluid medium.

2. A method according to claim 1, characterized in that it consists in characterizing the fluid medium (3) with the help of a photoelectric transducer (2) in which the semiconductor substrate (4) possesses at least one space charge zone (5) that is specially created in the semiconductor substrate from a diode type junction:

by creating photogenerated electric charges that diffuse towards the diode type junction on lighting through the fluid medium;

by recovering the photocurrents passing through the diode type junction and obtained from photogenerated electric charges of quantity that is determined by the rate of recombination at the interface (7) between the substrate and the fluid medium;

by creating a matrix of recovered photocurrent values; and by determining the electronic signature characteristic of the fluid medium from the created matrix of photocurrents.

3. A method according to claim 1, characterized in that it consists in characterizing the fluid medium (3) with the help of a photoelectric transducer (2) in which the semiconductor substrate (4) presents a space charge zone (5) that exists naturally at the surface of the semiconductor at the interface (7) between the substrate and the fluid medium, the substrate being provided with a first electrode (15) in contact with the fluid medium and with a second electrode (16) providing electrical contact with the face of the substrate that is opposite from the interface (7):

by recovering the photovoltage by performing capacitive measurements with the help of the first and second electrodes (15, 16);

by creating a matrix of recovered photovoltage values; and by determining the electronic signature characteristic of the fluid medium from the created matrix of photovoltages.

4. A method according to claim 1, characterized in that it consists in renewing the steps of lighting, of recovering the photoelectric magnitude, of creating the matrix, and of determining the electronic signature by modifying one and/or more of the following parameters: the application time of the lighting; the intensity of the lighting; the area of the lighting; the wavelength of the lighting; the temperature of the fluid medium and/or of the transducer; and applying an additional electric voltage to the transducer.

5. A method according to claim 1, characterized in that it consists in determining at least one visual image of the recovered values of the photoelectric magnitudes as an electronic signature characteristic of the fluid medium.

6. A method according to claim 5, characterized in that it includes a step of analyzing the electronic signature that consists in using quantitative methods of processing the images obtained.

7. A method according to claim 1, characterized in that it consists in subdividing the field over which the photoelectric magnitude varies into areas, with a color being allocated to each of them so that the electronic signature is a color image.

8. A method according to claim 1, characterized in that it consists in lighting the interface zone (7) with light flux (9) coming either from a single light beam that moves relative to the transducer in discrete or continuous manner, or else from at least one LED forming part of an array of LEDs that are selectively switched on and off.

9. A method according to claim 1, characterized in that it includes a step of analyzing the electronic signature in order to recognize the fluid medium and/or one or more of its individual components.

10. A method according to claim 9, characterized in that the analysis step consists in comparing the electronic signature of the fluid medium with at least one reference electronic signature determined for a known fluid medium.

11. A method according to claim 1, characterized in that it consists in performing a processing step on the reception surface prior to performing the lightning step.

12. A device for characterizing a fluid medium (3) with the help of a photoelectric transducer (2), the device being characterized in that it comprises:

at least one semiconductor substrate (4) possessing at least one space charge zone (5) and presenting a reception surface (6) for receiving the fluid medium in order to constitute an interface (7) between the substrate and the fluid medium;

a light beam production source (8) for producing a spot light beam (9) that is amplitude-modulated and that lights at least one zone of the interface (7) through the fluid medium (3);

a controller for controlling the spot light beam so as to light a plurality of zones of the interface (7) in succession;

a measurement system (10) for measuring values of a photoelectric magnitude delivered while performing the lighting so as to create a one- or two-dimensional matrix of values of the photoelectric magnitude; and a processor system (12) for processing values of the photoelectric magnitude delivered by the measurement system (10) and adapted to store the values of the photoelectric magnitude for each of the lighted zone of the interface (7) and, on the basis of the matrix, to determine an electronic signature characteristic of the fluid medium.

13. A device according to claim 12, characterized in that the light beam production source (8) for producing a spot light beam comprises either a spot light source optionally associated with a mover for moving the system for producing the spot light beam, or else an array of light-emitting diodes each subjected to on/off control.

14. A device according to claim 12, characterized in that the measurement system (10) for measuring the values of the photoelectric magnitude includes an external recovery circuit (14) comprising:

either a first electrode (15) placed on the face of the semiconductor substrate (4) forming the interface (7) and a second electrode (16) placed on the opposite face of the semiconductor substrate (4);

or a first electrode (15) and a second electrode (16) placed on the face of the semiconductor substrate (4) opposite from the face forming the interface (7);

or else an optically transparent first electrode (15) in contact with the fluid medium on one side and in contact on its opposite side with an optically transparent protective plate (22), and a second electrode (16) placed on the face of the semiconductor substrate (4) that is opposite from the face forming the interface (7).

15. A device according to claim 14, characterized in that the measurement system (10) also includes an optically transparent electrode (19) in contact with the fluid medium (3) and serving to apply a voltage between said electrode and an electrode placed on the face of the semiconductor substrate (4) opposite from its face forming the interface (7) so as to create matrices of photocurrent values for different values of the voltage applied between the electrodes.

16. A device according to claim 14, characterized in that the measurement electrodes (15, 16) provided on the face of the semiconductor substrate (4) opposite from a face forming the interface (7) are made in the form of interleaved combs.

17. A device according to claim 12, characterized in that the measurement system (10) performs simultaneous measurements of photocurrent values and of photovoltage values between the electrodes in order to make up pluri-dimensional matrices in order to establish a characteristic electronic signature of the fluid medium.

* * * * *